United States Patent
Henry et al.

(10) Patent No.: US 7,251,526 B2
(45) Date of Patent: Jul. 31, 2007

(54) ACTIVE IMPLANTABLE MEDICAL DEVICE OF THE DEFIBRILLATOR, CARDIOVERTOR AND/OR ANTITACHYCARDIA PACEMAKER TYPE, HAVING A HIGH MAXIMUM FREQUENCY FOR ANTIBRADYCARDIA STIMULATION

(75) Inventors: Christine Henry, Paris (FR); Laurence Graindorge, Chatenay Malabry (FR)

(73) Assignee: ELA Medical S.A.S., Montrouge (FR)

( * ) Notice: Subject to any disclaimer, the term of this patent is extended or adjusted under 35 U.S.C. 154(b) by 413 days.

(21) Appl. No.: 10/663,140

(22) Filed: Sep. 16, 2003

(65) Prior Publication Data

US 2004/0127943 A1    Jul. 1, 2004

(51) Int. Cl.
*A61N 1/365* (2006.01)

(52) U.S. Cl. ...................................... 607/14
(58) Field of Classification Search ............ 607/4–28
See application file for complete search history.

(56) References Cited

U.S. PATENT DOCUMENTS

| | | | | |
|---|---|---|---|---|
| 5,074,308 | A | * 12/1991 | Sholder et al. | 600/510 |
| 5,312,451 | A | 5/1994 | Limousin et al. | 607/15 |
| 5,458,622 | A | * 10/1995 | Alt | 607/15 |
| 5,462,060 | A | 10/1995 | Jacobson et al. | 128/702 |
| 5,868,793 | A | 2/1999 | Nitzche et al. | 607/5 |
| 5,882,352 | A | * 3/1999 | Duncan et al. | 607/4 |

FOREIGN PATENT DOCUMENTS

| | | |
|---|---|---|
| EP | 0 550 342 | 12/1992 |
| EP | 0 626 182 | 5/1994 |
| EP | 0 838 235 | 10/1997 |

* cited by examiner

*Primary Examiner*—Scott M. Getzow
(74) *Attorney, Agent, or Firm*—Orrick Herrington & Sutcliffe LLP

(57) ABSTRACT

An active implantable medical device of the defibrillator, cardiovertor and/or antitachycardia pacemaker type having a high maximum frequency for antibradycardia stimulation. This device provides antibradycardia stimulation at a stimulation frequency that has a programmed maximum stimulation frequency. For a detected rate exceeding a given frequency threshold, the device analyzes the cardiac activity to discriminate a ventricular tachycardia or fibrillation to command in consequence an appropriate antitachycardia therapy. The maximum stimulation frequency for antibradycardia is higher than the given frequency threshold for the antitachycardia analysis, and the cardiac rhythm is analyzed to detect a particular succession of events that are likely to reveal the presence or the appearance of a ventricular tachycardia during such high antibradycardia stimulation. In this case, the duration of the ventriculo-atrial delay of stimulation is prolonged at least until the end of the calculated escape interval, and until the end of the programmed maximum interval of detection of ventricular tachycardia. This accommodates an antibradycardia stimulation at a rate greater than the frequency threshold used to suspect or declare an antitachycardia while enabling detection of the latter.

9 Claims, No Drawings

ACTIVE IMPLANTABLE MEDICAL DEVICE OF THE DEFIBRILLATOR, CARDIOVERTOR AND/OR ANTITACHYCARDIA PACEMAKER TYPE, HAVING A HIGH MAXIMUM FREQUENCY FOR ANTIBRADYCARDIA STIMULATION

FIELD OF THE INVENTION

The present invention relates to active implantable medical devices (within the meaning of the Jun. 20, 1990 directive 90/385/CEE of the Council of the European Communities), and more particularly to the family of the devices that deliver to the heart shock pulses of high energy (i.e., pulses having an energy that notably exceeds the energy typically provided for simple stimulation of cardiac activity) in order to terminate a tachyarrhythmia. These modes of antitachycardia therapy include also a mode of programmed high frequency stimulation or "ATP" (AntiTachycardia Pacing). These devices are commonly called "implantable defibrillators" or "cardioversion devices." It should be understood, however, that the invention is also applicable to combinations of these devices such as implantable defibrillators/cardiovertors/pacemakers and implantable defibrillators/pacemakers.

BACKGROUND OF THE INVENTION

The decision to apply an antitachycardia therapy, and the choice of which therapy to apply (e.g., shock or ATP stimulation) is operated by an algorithm that performs a detection and classification of the various tachyarrhythmia according to several criteria, mainly according to the ventricular frequency, but also according to the stability of the ventricular intervals, the stability of atrio-ventricular conduction, the mode of starting or chamber of origin of the tachycardia, etc. (see in particular the EP-A-0 626 182 and its corresponding U.S. Pat. No. 5,462,060 and EP-A-0 838 235 and its corresponding U.S. Pat. No. 5,868,793 commonly assigned herewith to ELA Médical).

The ventricular frequency is the first criterion that makes it possible in particular to distinguish three situations relevant to the tachycardia detection and classification algorithm:

1. A detected frequency that is lower than a given frequency threshold, called "frequency of detection of VT (ventricular tachycardia)", for example, about 140 bpm. The aforementioned algorithm considers that this ventricular rate is slow, but is not pathological, and never justifies the application of an antitachycardia therapy.
2. A detected frequency which is between the frequency of detection of VT, typically 140 bpm, and a higher frequency called the "frequency of detection of VF (ventricular fibrillation)", typically at about 200 bpm. The algorithm considers in this range that there is "suspicion of VT" and carries out a more thorough analysis, implementing criteria other than just the ventricular frequency. This more thorough analysis proceeds to determine more precisely the type of disorder and to decide whether it is necessary to apply a therapy, and if so what therapy (shock or ATP stimulation) to apply;
3. A detected frequency that is higher than the frequency of detection of VF, typically 200 bpm. The algorithm considers in this case that the application of a therapy is always necessary and to be delivered without delay.

The above-mentioned implantable devices typically include, in addition to the antitachycardia therapy means described, means (e.g., detection circuits, stimulation circuits, and associated control logic) for providing antibradycardia stimulation therapy. Antibradycardia stimulation allows, as with a traditional demand implantable pacemaker, delivery if necessary of stimulation pulses to the ventricle (and possibly to the atrium) in the absence of a detected spontaneous depolarization of the relevant cavity.

Antibradycardia stimulation is preferably operated at a variable frequency, depending on the activity of the patient. In this regard, the pacemakers can be equipped with one or more suitable activity sensors that may be physiological (for example, minute-ventilation sensor) or physical (for example, acceleration), as known in the art, making it possible to evaluate the instantaneous cardiac output requirements and/or physical activity level of the patient and to control consequently the stimulation frequency in a rate responsive manner. This is known in the art as pacing using a function of enslavement (to the patient activity) or rate responsive pacing. Thus, when the patient is exerting an "effort", i.e., engaging in activity other than resting, the activity sensor provides a corresponding measure that is used by the control logic to increase the stimulation frequency (and to lower the given frequency as the effort level is reduced accordingly). This enables the patient to support hemodynamically the greater effort. Of course, this variable stimulation frequency is typically provided with a maximum limit, a value known as the "maximum stimulation frequency". This limit value is typically programmed by the physician at the time of the implantation of the device or during follow-up visits by the patient.

It has been discovered that a particular situation arises when the maximum stimulation frequency for antibradycardia can be programmed at a value that is higher than the threshold frequency of detection of the VT for antitachycardia. In this case, for high values of the stimulation frequency, the device considers that this high rate is a sinusal tachycardia (ST), because the rate is in 1:1 association, stable and without acceleration. But it can happen that a VT begins while at the same time the patient is in a situation of effort where the patient is stimulated by the device at a relatively high frequency, undergoing antibradycardia therapy.

The frequency of the VT and that of stimulation can be close so that atrial stimulation can mask the spontaneous R waves. This might lead to a delay in the detection of the VT or to an under-detection of the VT. As a result, there can be a less than optimal delivery of the antitachycardia therapy that would be appropriate. Indeed, it may lead to a delay in antitachycardia therapy that can reach several minutes.

Of course, to avoid this issue, physicians have been known to program the maximum stimulation frequency to a value that is lower than the frequency of detection of VT. But this has the disadvantage of limiting the maximum frequency at which the patient can be appropriately stimulated. For example, in the solution above, where the frequency of detection of VT is set at 140 bpm, this has resulted in limiting the maximum stimulation frequency to 140 bpm. It would be desirable, however, particularly for younger patients, to increase the maximum stimulation frequency to allow them to obtain comfortably a greater level of effort, for example, up to 180 bpm.

OBJECTS AND SUMMARY OF THE INVENTION

One of the objects of the present invention is to avoid such a situation, while also preventing a stimulation (atrial or ventricular) from masking a spontaneous ventricular event in the event of suspicion of VT, in order to be able to carry out without delay the diagnosis of VT, thereby to ensure as soon as possible the VT detection and the treatment.

It is also an object of the present invention to provide an antibradycardia stimulation therapy that is able to reach a high stimulation rate without compromising the diagnosis and the treatment of possible VT.

The active implantable medical device for which the present invention is applicable is a defibrillator or cardio-vertor of the type in itself known, as described, for example, by the above-mentioned EP-A-0 838 235 and corresponding U.S. Pat. No. 5,868,793, i.e., including means for sensing the ventricular and atrial cardiac activity, means for delivering antitachycardia therapy based on an analysis of cardiac activity and able to apply an antitachycardia therapy such as one or more of a defibrillation shock, a cardioversion shock, and an antitachycardia pacing (ATP) stimulation, and means for delivering antibradycardia stimulation pulses based on analysis of cardiac activity and able to deliver ventricular and/or atrial stimulation pulses at a rate responsive stimulation frequency determined by the device according to the detected activity of the patient. This stimulation frequency is limited to a programmed maximum stimulation frequency, and the frequency of the delivered pulses is defined according to a calculated escape interval ("EI") including an atrio-ventricular delay ("AVD") and a ventriculo-atrial delay ("VAD"). It is further envisaged that the device includes a first means for analyzing cardiac activity implemented when the detected frequency of ventricular cardiac activity is higher than a given threshold frequency for the antitachycardia analysis, and able to recognize and discriminate the presence of a ventricular tachycardia, or a ventricular fibrillation, and to command consequently the means for antitachycardia therapy to deliver an appropriate therapy.

According to the present invention, the aforementioned programmed maximum stimulation frequency is set to be higher than the given threshold frequency of analysis, and also provided is a second means for analyzing the cardiac activity to detect a particular succession of events likely to reveal the presence or the appearance of a ventricular tachycardia, and that is able to prolong the duration of the aforesaid ventriculo-atrial delay (VAD) at least until the end of the longer of (i) the aforesaid calculated escape interval ("EI"), and (ii) a programmed maximum interval of detection of ventricular tachycardia (corresponding to the aforementioned threshold frequency of analysis (i.e., the threshold of detection of the VT or "TDI")), increased by a delay of tolerance $\Delta$ of a few milliseconds (VAD=Max{EI; TDI+$\Delta$}).

In a preferred embodiment, the second means for analyzing the cardiac activity is able to detect:

(1) an occurrence of a ventricular extrasystole, and/or
(2) an occurrence of a ventricular event presenting a coupling interval that is less than or equal to that of the programmed maximum interval of detection of ventricular tachycardia, in the presence of a proven acceleration of rate having a ventricular origin, and/or
(3) an occurrence of a ventricular event presenting a coupling interval less than or equal to the programmed maximum interval of detection of ventricular tachycardia, in the presence of a ventricular extrasystole preceding this event, the duration of the aforesaid coupling interval being equal to the duration separating the extrasystole from the ventricular event within a given tolerance factor, and/or
(4) a presence of a confirmed ventricular tachycardia rate.

More preferably, the second analyzing means is able to prolong the duration of the aforesaid ventriculo-atrial delay until the later of one of two times corresponding, on the one hand, to the end of the calculated escape interval and, on the other hand, to the end of the programmed maximum interval of detection of ventricular tachycardia, increased by a predetermined safety factor, in particular by a programmed fixed duration.

When the means for antibradycardia stimulation delivers atrial stimulation pulses synchronous with a ventricular extrasystole, the second analyzing means is advantageously able to prolong the duration of the atrial escape interval started on a synchronous atrial stimulation, this prolongation being maintained until the later of two times corresponding, on the one hand, to the end of the interval of the calculated atrial escape and, on the other hand, to the end of the programmed maximum interval of detection of ventricular tachycardia, increased by a predetermined safety factor.

When the means for delivering antibradycardia stimulation operates in a standard VVI mode, the second analyzing means is advantageously able to prolong the duration of the ventricular escape interval started on a ventricular event presenting a coupling interval (R-R interval or V-R interval) lower than the programmed maximum interval of detection of ventricular tachycardia, and in the presence of an acceleration of the rate having a ventricular origin, this prolongation being maintained until the later of the two times corresponding, on the one hand, to the end of the calculated ventricular escape interval and, on the other hand, to the end of the programmed maximum interval of detection of ventricular tachycardia, increased by a predetermined safety factor.

DETAILED DESCRIPTION OF THE INVENTION

A detailed embodiment of a preferred implementation of the present invention now will be discussed.

Preliminarily, the following definitions are used in the description below:

Detection P: sensing of spontaneous activity having its origin in the atrium.

Detection R: sensing of spontaneous activity having its origin in the ventricle.

Stimulation A: a stimulation pulse delivered in the atrium.

Stimulation V: a stimulation pulse delivered in the ventricle.

Atrial event: detection P or stimulation A;

Ventricular event: detection R or stimulation V;

Cardiac cycle: an interval of time separating two events of comparable nature in the same cavity, for example, separating two detections P, or two stimulations A, or two detections R, or two stimulations V.

Escape Interval (EI): an interval of time, counted after a detection or a stimulation in a given cavity, following which a stimulation is to be delivered in this cavity if no spontaneous event were detected in this same cavity. The escape interval is composed of the successive of the atrio-ventricular time (AVD) and the ventriculo-atrial delay (VAD): IE=AVD+VAD.

Ventricular extrasystole (VES): one defines three types of VES:

(i) VES of first type (VES1): a simple ventricular extrasystole, i.e., detection R without a preceding associated detection P, in a given interval of time, typically between 31 and 300 ms;

(ii) VES of second type (VES2): detection R preceded by a detection P or a stimulation V, with a coupling interval (R-R interval or V-R interval) that is less than or equal to a parameterized value, for example 75%, of the average PP—i.e., a coupling interval that is less than or equal to the programmed maximum interval of detection of ventricular tachycardia, in the presence of a proven acceleration of the rate having a ventricular origin; and (iii) VES of third type (VES3): a ventricular event presenting a coupling interval that is less than or equal to the programmed maximum interval of detection of ventricular tachycardia, in the presence of a VES preceding this event, the duration of this coupling interval being equal, with a given factor of tolerance, to the duration separating the VES from the ventricular event.

For further details regarding the identification of extrasystoles, reference is made to the EP-A-0 550 342 and its corresponding U.S. Pat. No. 5,312,451 commonly assigned herewith to Ela Médical, which describes an algorithm of detection and treatment of the VES and which U.S. Pat. No. 5,312,451 is incorporated herein by reference.

The present invention can be implemented starting from the available known detection and classification algorithm and described in the EP -A-0 626 182 and EP-A-0 838 235 and the respective U.S. Pat. Nos. 5,462,060 and 5,868,793 above-mentioned, which U.S. Patents are incorporated herein by reference in their entirety and which algorithm is used by the commercially available Defender™ and Alto™ models of defibrillators of ELA Médical, to operate the detection and the classification of the various tachyarrhythmia according to various criteria. This algorithm makes it possible in particular to detect and confirm the occurrence of VT by an analysis of the cardiac activity, this analysis being implemented as soon as the ventricular frequency of the sensed rhythm exceeds a programmed frequency threshold known as "frequency of detection of VT". It is in particular possible to discriminate, between various disorders, those which authorize the application of an antitachycardia therapy (a proven slow or rapid VT, FV), and, in addition, those disorders that are not of ventricular origin, for which any antitachycardia therapy of this type must be inhibited (supra-ventricular tachycardia ("SVT"), sinusal tachycardia ("ST") and similar disorders (one will be able to refer to the above-mentioned patents for further details)).

In addition, the device includes an antibradycardia stimulation means, i.e., it allows a traditional cardiac demand pacemaker operation, by authorizing a stimulation frequency able to reach a "maximum stimulation frequency".

The invention is directed to the particular situation where the maximum stimulation frequency can be adjusted to a value (for example, 180 bpm) that is higher than the minimal or threshold frequency of detection of the VT (for example, 140 bpm). The invention aims at preventing an antibradycardia stimulation, atrial or ventricular, from masking a spontaneous ventricular event in the event of a suspicion of VT, so as to ensure a fast detection and treatment of a determined VT.

To this end, when the implantable device functions in dual-chamber operating mode, it prolongs if necessary the atrio-ventricular delay ("AVD") so that the AVD finishes at the time corresponding to the later of:

1. the end of the calculated escape interval: Calculated EI can be the base escape interval, or it can be given by a function of enslavement (i.e., a rate responsive) of the pacemaker, or even by functions of smoothing, or prevention, or a combination of these functions, this in a way that is known to persons of ordinary skill in the art; or 2. the end of the programmed maximum interval of detection of VT (in general, this is the interval of detection of slow VT, corresponding to the minimal frequency of detection of the VT), increased by a safety margin (for example, a programmable value, typically 31 ms), to ensure the detection of a VT exactly at the frequency of detection of the VT). This possible prolongation of the AVD is operated for one cycle only, and the following cycle the algorithm again carries out an evaluation of the situation.

It is started when certain events occur that give rise to a suspicion of a starting or a presence of VT (if not, a stimulation would not have been there). The prolongation of the AVD can thus be operated on one or more following criteria:

1. VES of the type ESV1, i.e., presence of a ventricular detection not preceded by an atrial event within a physiological time (typically 31 to 300 ms), and/or 2. ESV of the type ESV2, i.e., presence of a ventricular event presenting a coupling interval less than or equal to the longest interval of detection of VT programmed (thus corresponding to the minimal frequency of detection of VT), with detection of an acceleration of ventricular origin (the criterion of analysis of the acceleration of the ventricular rhythm and the determination of the origin of this acceleration, ventricular or atrial, are described in the above-mentioned EP-A-0 626 182), and U.S. Pat. No. 5,462,060 and/or 3. ESV of the type ESV3, i.e., detection of a ventricular event presenting a coupling interval less than or equal to the longest interval of detection of VT programmed, preceded by a VES and with a coupling interval close (with typically±31 ms) to this VES, and/or 4. confirmed detection of a rate of VT (in accordance with the mode of analysis of the EP-A-0 838 235 and U.S. Pat. No. 5,868,793, for example).

In addition to this general case, other particular cases can arise that are desirable to take into account. Thus, with a VES, one can envision a synchronous atrial stimulation to prevent a retrograde conduction. In this case, it is the atrial escape interval AEI (i.e., A-A delay) started on this atrial stimulation, which is prolonged to finish at the time corresponding to later of:

1. the end of the calculated atrial escape interval; and 2. the end of the maximum programmed interval of VT detection, increased by a safety margin.

In addition, in the case of a dual-chamber pacemaker, when the pacemaker operates in the VVI mode and a detected ventricular event occurs presenting a coupling interval less than the interval of detection of VT and an acceleration of ventricular origin (as explained above), in order not to stimulate the ventricle too early it is the ventricular escape interval which is prolonged, so as to end at the time corresponding to later of:

1. the end of the calculated ventricular escape interval; and 2. the end of the programmed maximum interval of detection of VT, increased by a safety margin.

Suitable devices for which the present invention has application include, for example, the Defender™ and Alto™ brand of defibrillators available from Ela Médical, Montrouge, France. These devices are microprocessor-based systems having known circuits for receiving, conditioning and processing detected electrical signals originating in the cavities, and are capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. Similarly, the detection circuits used to detect the cardiac signals in the atrium and the ventricle in the left and/or right chambers, as well as the circuits for delivering simple cardiac stimulation to one or more cardiac chambers and for delivery ATP and shock stimulation therapies of controllable energy levels, are well known, and any suitable design thereof may be used.

One skilled in the art will appreciate that the present invention can be practiced by other than the described embodiments, which are presented for purposes of illustration and not of limitation.

We claim:

1. An active implantable medical device of the defibrillator, cardiovertor and/or implantable antitachycardia pacemaker type, including:

means for sensing ventricular and atrial cardiac activity;

means for delivering an antitachycardia therapy able to apply selectively a defibrillation shock, a cardioversion shock and an antitachycardia pacing stimulation;

means for detecting patient activity;

means for delivering antibradycardia stimulation able to deliver ventricular and atrial stimulation pulses at a stimulation frequency determined according to detected patient activity, said stimulation frequency having a maximum stimulation frequency, the stimulation pulses being delivered at a rate defined according to a calculated escape interval including an atrioventricular delay and a ventriculo-atrial delay;

first means for analyzing the detected cardiac activity with respect to a given threshold frequency of analysis and determining a frequency of cardiac activity and when the determined frequency of ventricular cardiac activity is greater than said given threshold frequency of analysis, said first analyzing means being able to recognize and discriminate the presence of a ventricular tachycardia and a ventricular fibrillation, said means for delivering antitachycardia therapy being responsive to a detected ventricular tachycardia or a detected ventricular fibrillation by delivering an appropriate antitachycardia therapy;

wherein said antibradycarda therapy means further comprises said maximum stimulation frequency being higher than said threshold frequency of analysis; and second means for analyzing the cardiac activity and detecting in said cardiac activity a particular succession of events corresponding to a presence or an appearance of a spontaneous ventricular tachycardia, said second analyzing means further comprising means for prolonging the duration of the ventriculo-atrial delay until the later of the end of said calculated escape interval and the end of a programmed maximum interval of detection of ventricular tachycardia corresponding to the aforementioned threshold frequency of analysis increased by a tolerance delay.

2. The device of claim 1, wherein the second analyzing means further comprises means for detecting the particular succession of events as an occurrence of a ventricular extrasystole.

3. The device of claim 2, wherein said first analyzing means comprises means for identifying an acceleration of a ventricular frequency that is ventricular in origin, and said second analyzing means further comprises means for detecting the particular succession of events as an occurrence of a ventricular event presenting a coupling interval less than or equal to the maximum interval of detection of ventricular tachycardia, in the presence of a proven acceleration of the rate having a ventricular origin.

4. The device of claim 2, wherein the second analyzing means further comprises means for detecting the particular succession of events as a coupling interval between ventricular events and an occurrence of a ventricular event presenting a coupling interval less than or equal to the maximum interval of detection of ventricular tachycardia, in the presence of a ventricular extrasystole preceding said ventricular event, the duration of said coupling interval being equal to a duration separating the extrasystole from the ventricular event within a given tolerance factor.

5. The device of claim 2, wherein the antibradycardia stimulation delivery means further comprises means for delivering atrial stimulation pulses synchronous to a ventricular extrasystole, and the second analyzing means further comprises means for prolonging the duration of the atrial escape interval started on a synchronous atrial stimulation, said prolongation being maintained until the later of the end of the calculated atrial escape interval and the end of the programmed maximum interval of detection of ventricular tachycardia increased by a predetermined safety factor.

6. The device of claim 1, wherein the second analyzing means further comprises means for detecting a presence of a confirmed rate of ventricular tachycardia.

7. The device of claim 1, wherein the second analyzing means further comprises means for prolonging the duration of said aforesaid ventriculo-atrial delay until the later of one of the end of the calculated escape interval and the end of the programmed maximum interval of detection of ventricular tachycardia increased by a predetermined safety factor.

8. The device of claim 7, wherein said predetermined safety factor is a programmed fixed duration.

9. The device of claim 1, wherein the antibradycardia stimulation delivery means operates in a mode VVI and the second analyzing means further comprises means for prolonging the duration of the ventricular escape interval started on a ventricular event presenting a coupling interval less than the programmed maximum interval of detection of ventricular tachycardia, and in the presence of an acceleration of the rate having a ventricular origin, said prolongation being maintained until the later of the end of the calculated ventricular escape interval and the end of the programmed maximum interval of detection of ventricular tachycardia increased by a predetermined safety factor.

* * * * *